(12) United States Patent
Eguchi et al.

(10) Patent No.: US 9,795,553 B2
(45) Date of Patent: Oct. 24, 2017

(54) HIGHLY FUNCTIONAL COLORING MATERIAL AND PRODUCTION PROCESS FOR THE SAME

(71) Applicant: MITSUBISHI PENCIL COMPANY, LIMITED, Shinagawa-ku (JP)

(72) Inventors: Tamotsu Eguchi, Fujioka (JP); Satoshi Sakuma, Fujioka (JP)

(73) Assignee: MITSUBISHI PENCIL COMPANY, LIMITED, Tokyo (JP)

( * ) Notice: Subject to any disclaimer, the term of this patent is extended or adjusted under 35 U.S.C. 154(b) by 214 days.

(21) Appl. No.: 14/308,982

(22) Filed: Jun. 19, 2014

(65) Prior Publication Data
US 2014/0377314 A1 Dec. 25, 2014

(30) Foreign Application Priority Data
Jun. 21, 2013 (JP) .................. 2013-130549

(51) Int. Cl.
| | |
|---|---|
| *A61K 8/02* | (2006.01) |
| *A61K 8/85* | (2006.01) |
| *A61Q 1/02* | (2006.01) |
| *A61K 8/81* | (2006.01) |
| *A61K 8/19* | (2006.01) |
| *A61K 8/29* | (2006.01) |

(52) U.S. Cl.
CPC .............. *A61K 8/85* (2013.01); *A61K 8/0254* (2013.01); *A61K 8/19* (2013.01); *A61K 8/29* (2013.01); *A61K 8/8147* (2013.01); *A61Q 1/02* (2013.01); *A61K 2800/412* (2013.01); *A61K 2800/61* (2013.01)

(58) Field of Classification Search
CPC .......... A61K 8/25; A61K 8/152; A61K 8/891; A61K 8/585; A61K 8/898; A61K 8/23; A61K 8/00; A61K 8/29; A61K 8/897; A61K 2800/594
See application file for complete search history.

(56) References Cited

U.S. PATENT DOCUMENTS

| | | |
|---|---|---|
| 2008/0279899 A1 | 11/2008 | Geffroy et al. |
| 2009/0142380 A2 | 6/2009 | Geffroy et al. |
| 2012/0276178 A1 | 11/2012 | Sakuma et al. |
| 2013/0052246 A1 | 2/2013 | Ito et al. |

FOREIGN PATENT DOCUMENTS

| | | | | |
|---|---|---|---|---|
| CN | 101125117 A | 2/2008 | | |
| CN | 102791244 A | 11/2012 | | |
| JP | 2003-40736 A | 2/2003 | | |
| JP | 2003-10840 A | * | 4/2003 | ............... A61K 7/02 |
| JP | 2003-104840 A | 4/2003 | | |
| WO | WO 2011/137938 A1 | 11/2011 | | |

* cited by examiner

*Primary Examiner* — Nannette Holloman
(74) *Attorney, Agent, or Firm* — Buchanan, Ingersoll & Rooney PC

(57) ABSTRACT

The present invention relates to a highly functional coloring material which causes less separation between a pigment and tabular inorganic powders and brings about less color separation and which is obtained by coating evenly a pigment on the surfaces of tabular colorless to white inorganic powders via a specific binder resin. The coloring material of the present invention does not bring about color deviation and color separation.

7 Claims, 1 Drawing Sheet

HIGHLY FUNCTIONAL COLORING MATERIAL AND PRODUCTION PROCESS FOR THE SAME

This nonprovisional application claims priority under 35 U.S.C. §119(a) on Patent Application No. 2013-130549 filed in Japan on 21 Jun. 2013, the entire contents of which are hereby incorporate by reference.

BACKGROUND OF THE INVENTION

Field of the Invention

The present invention relates to a highly functional coloring material which is used for cosmetics and the like and which has an excellent feel, and a production process for the same.

Description of Related Art

Organic pigments and inorganic pigments of an iron oxide base have so far been used as coloring materials for cosmetics such as foundations, cheeks, eyeshadows and the like. Further, micas, BN (boron nitride) and the like which are tabular inorganic powders are mixed therewith for the purpose of improving the feel of the cosmetic. In general, pigments of plural colors such as red, yellow and black, and tabular inorganic powders are mixed with vehicles in order to display optional color tones and use feelings, and the mixtures pass through processes such as dispersion, emulsion and the like, whereby cosmetics are produced.

However, the surfaces of coloring materials have individually different properties and are different as well in the forms and the sizes of particles, and therefore it is difficult to evenly control them. Also, there has so far been involved therein the problem that the coloring materials are not evenly spread when they are applied on the skin and that they change in color tones depending on the manner of application. Further, there has so far been involved as well the problem that when a tabular inorganic powder is added in order to improve the feel, the coloring material and the tabular inorganic powder are present separately, so that a satisfactory effect is not obtained.

It is disclosed in Japanese Patent No. 3770536 as a conventional technology for solving the above problems that spherical particles formed by using tabular boron nitride having a fixed form and inorganic powders having a fixed average particle diameter as essential components are broken by applying a suitable pressure such as pressing with fingers and the like to return the boron nitride to the original tabular form and that a homogeneous cosmetic film can be provided by blending the above spherical powders with the cosmetics.

Further, it is disclosed in JP-A 2003-104840 that blending boron nitride which is processed on a surface with metal soap improves the adhesion of the cosmetic onto the skin and the holding of the cosmetic on the skin while maintaining merits of boron nitride such as good sliding, brightness and the like and that the skin is endowed with a natural gloss in finishing.

PRIOR ART DOCUMENTS

Patent document 1: Japanese Patent No. 3770536
Patent document 2: JP-A 2003-104840

However, the problems described above have not yet come to be sufficiently solved by such the conventional technologies as described above.

BRIEF SUMMARY OF THE INVENTION

In light of the problems and the like on the conventional technologies described above, the present invention intends to solve them, and an object thereof is to provide a highly functional coloring material which is used for cosmetics and the like and which is excellent in a use feeling.

In light of the conventional problems and the like described above, intense researches repeated by the present inventors have resulted in coming to complete the present invention by coating evenly a pigment on the surfaces of colorless to white inorganic powders via a binder resin.

That is, the present invention comprises the following items (1) to (9).

(1) A highly functional coloring material characterized by coating evenly a pigment on the surfaces of tabular colorless to white inorganic powders via a binder resin.
(2) The highly functional coloring material as described in the above item (1), wherein the tabular colorless to white inorganic powder is mica or BN (boron nitride).
(3) The highly functional coloring material as described in the above item (1), wherein the binder resin is soluble in ethanol and insoluble in water.
(4) The highly functional coloring material as described in the above item (3), wherein the binder resin is a carboxy betaine resin.
(5) The highly functional coloring material as described in the above item (1), wherein the binder resin is an alkali-soluble type acryl resin.
(6) The highly functional coloring material as described in the above item (1), wherein the coloring material is an organic pigment, iron oxide, carbon black or fine particle titanium oxide.
(7) The highly functional coloring material as described in the above item (1), wherein pigments of plural colors are coated on the surfaces of the tabular colorless to white inorganic powders.
(8) A production process for the highly functional coloring material as described in the above item (1), characterized by comprising the steps of:
mixing a pigment, a binder resin and a vehicle,
dispersing evenly the mixture by means of a disperser such as a bead mill and the like,
then adding tabular inorganic powders to the dispersion and mixing them while stirring and
taking out the colored tabular inorganic powders by centrifugal separation or filtering and drying and crushing them.
(9) A production process for the highly functional coloring material as described in the above item (1), characterized by comprising the steps of:
mixing a pigment, a binder resin and a vehicle,
dispersing evenly the mixture by means of a disperser such as a bead mill and the like,
then adding tabular inorganic powders to the dispersion and mixing them while stirring and
drying the dispersion by means of a spray dryer.

According to the present invention, a highly functional coloring material having an excellent use feeling is obtained, and when it is used for cosmetics such as foundations, cheeks, eyeshadows and the like, the cosmetics can be improved in a functionality such as a spreading property, a color irregularity, an adhesive property and the like. Further, even the colored tabular inorganic powders alone can be adhered on a skin, and therefore they can be used as they are in the form of a cosmetic to which an oil and fat component, a surfactant, a preservative and the like are not required to be added.

BRIEF DESCRIPTION OF THE SEVERAL VIEWS OF THE DRAWING(S)

FIG. 1 is an electron micrograph of the colored tabular inorganic powders obtained in the present invention. A state in which iron oxide (red pigment) is coated evenly on the surface of BN (boron nitride) via a binder can be observed.

DETAILED DESCRIPTION OF THE INVENTION

The embodiments of the present invention shall be explained below in detail.

The colorless to white tabular inorganic powders which are the base material of the present invention are selected from mica and BN (boron nitride) which are usually used for cosmetics. Since the above powders are tabular and have a laminated structure, the laminated layer is broken when they are coated on a skin and spread with fingers, whereby a dry and smooth touch feeling is obtained, and therefore an optimum amount thereof is blended in many cases. However, while a particle diameter of the tabular inorganic powders is 1 to 100 μm, that of pigments is 0.1 to 1 μm, and they are different in a particle diameter to a large extent. Accordingly, even if a cosmetic is controlled to a prescribed color tone (for example, light beige) on the whole, the color tone is liable to change (color change and white powder residue) when the cosmetic is applied and spread with fingers. The above matters are not preferable for finishing makeup.

Investigations have been repeated by the present inventors in order to improve the problems described above based on the assumption that a coloring material which is prevented from color separation without damaging the functions (sliding, spreading and the like) of the tabular particles is obtained by coating a pigment thinly and evenly on the surfaces of the tabular inorganic powders, and they have resulted in finding that the targeted colored tabular inorganic powders are obtained by dispersing a pigment via a specific binder resin and mixing the dispersion with the tabular inorganic powders.

The tabular inorganic powders used in the present invention are preferably colorless to white from the viewpoint of the object thereof, and mica and BN (boron nitride) which are usually used for cosmetic applications are preferably used.

Particularly when great importance is put on sliding and spreading, BN (boron nitride) is preferably used.

In this connection, the term "colorless to white" means any of transparent, translucent, turbid or white, and it includes a state in which light completely passes, a state in which light partially passes and a state in which light does not pass at all. Also, the colorless to white tabular inorganic powders may be colored as long as the effects of the pigment used in the present invention are not damaged.

BN (boron nitride) SHP-3, SHP-7 and the like manufactured by Mizushima Ferroalloy Co., Ltd. can be used as a commercially available product.

Pigments for use in ordinary cosmetics can be used as the pigment adhered on the surfaces of the tabular inorganic powders. Capable of being used are, for example, Tarox BL-100P (iron oxide black, manufactured by Titan Kogyo, Ltd.), Tarox R516L (iron oxide red, manufactured by Titan Kogyo, Ltd.), Tarox LLXLO (iron oxide yellow, manufactured by Titan Kogyo, Ltd.), Red No. 204 (organic pigment red, manufactured by Kishi Kasei Co., Ltd.), Yellow No. 4 aluminum lake (organic pigment yellow, manufactured by Kishi Kasei Co., Ltd.) and the like.

It is important for dispersing evenly the pigment and adhering it on the surfaces of tabular inorganic powders to select the binder resin, and it is the basis of the technology according to the present invention. Required as the performances of the binder resin are three factors of (1) finely dispersing the pigment and stabilizing it, (2) adhering the pigment on the surfaces of the tabular inorganic powders and (3) no elution of the pigment by water and oil & fat. Various investigations therefor have resulted in finding a binder resin which is soluble in ethanol and insoluble in water in order to complete the present invention. To be specific, a carboxy betaine resin which is dissolved in ethanol is used as the binder resin.

Also, the same effect can be obtained as well by using an alkali-soluble type acryl resin as another means. To be specific, the alkali-soluble type acryl resin is added to water, and the solution is controlled to a pH of 7 to 9 by a pH controlling agent such as ammonia and the like, whereby the resin solution can be obtained. The targeted colored powders can be obtained by dispersing the pigment in the above solution, adding the tabular inorganic powders to the dispersion and stirring it and then drying it.

The additional characteristic of the present invention includes that plural colors and kinds of pigments can be adhered on the surfaces of the tabular inorganic powders. Usually, a foundation is colored by mixing white, black, red and yellow pigments in order to meet the skin colors of various persons, and brought about in a certain case are defects such as delicate color deviation depending on the state of dispersing the pigment, a difference between the solution color and the coated color (color developed by spreading the cosmetic with fingers) and a change in the color tone and the glossiness caused by sweating. The pigment solutions of the respective colors comprising the pigment, the binder resin and the vehicle are prepared in the present invention, and they can be mixed to control the mixture to a prescribed color tone. The tabular inorganic powders are added to the above preparations and stirred, whereby the pigments of the plural colors can be adhered on the surfaces of the tabular inorganic powders. In this case, a unit of the tabular inorganic powders is provided with a prescribed color tone, and therefore color deviation and a change in the coated color can be less liable to be brought about.

EXAMPLES

Next, the present invention shall be explained in further details with reference to examples, but the present invention shall not be restricted to the examples described below.

Example 1

| | |
|---|---|
| Tarox R516L (iron oxide red, manufactured by Titan Kogyo, Ltd.) | 20.0% by mass |
| Yukaformer R202 (carboxy betaine resin, manufactured by Mitsubishi Chemical Corporation) | 10.0% by mass |
| Ethanol | 70.0% by mass |

The above components were mixed while stirring, and then the pigment was dispersed evenly by means of a bead mill, whereby a pigment dispersion (Red 1) was obtained.

| | |
|---|---|
| Pigment dispersion (Red 1) | 10.0% by mass |
| Ethanol | 60.0% by mass |
| Boron nitride (SHP-3, manufactured by Mizushima Ferroalloy Co., Ltd. | 30.0% by mass |

The above components were mixed while stirring, and then the supernatant was removed by centrifugal separation to take out colored boron nitride.

Ethanol 40.0% by mass was added to the colored boron nitride 10.0% by mass taken out, and the mixture was subjected again to stirring and centrifugal separation, whereby the pigment which was not adhered on boron nitride was removed. Then, the mixture was dried and crushed, whereby the targeted colored boron nitride could be obtained.

Example 2

| | |
|---|---|
| Tarox LLXLO (iron oxide yellow, manufactured by Titan Kogyo, Ltd.) | 20.0% by mass |
| Luvimer 100P (alkali-soluble type acryl resin, manufactured by BASF A.G. | 4.0% by mass |
| Water | 76.0% by mass |

A suitable amount of a pH controlling agent was mixed with the above blended components while stirring so that a pH was controlled to 8, and then the pigment was dispersed evenly by means of a bead mill, whereby a pigment dispersion (Yellow 1) was obtained.

| | |
|---|---|
| Pigment dispersion (Yellow 1) | 10.0% by mass |
| Water | 60.0% by mass |
| Boron nitride (SHP-7, manufactured by Mizushima Ferroalloy Co., Ltd. | 30.0% by mass |

The above components were mixed while stirring, and then the supernatant was removed by centrifugal separation to take out colored boron nitride.

Water 40.0% by mass was added to the colored boron nitride 10.0% by mass taken out, and the mixture was subjected again to stirring and centrifugal separation, whereby the pigment which was not adhered was removed. Then, the mixture was dried and crushed, whereby the targeted colored boron nitride could be obtained.

Evaluation

Water was added to the colored boron nitrides obtained in Example 1 and Example 2, and the mixtures were stirred and then left standing for a whole day and night. To observe water after left standing, it stayed colorless and transparent, and it could be confirmed that the pigment was not eluted from the boron nitride. Further, the colored boron nitride formed by the method described above was added to a conventional foundation preparation to find that a cosmetic which was free of color deviation and which was well spread by light touch with fingers could be obtained. In addition thereto, the colored boron nitride formed was coated on a skin as it was in the form of the powders to find that it could be used as a powder foundation which was well spread in a thin layer.

A highly functional cosmetic which is well spread and brings about less color deviation and less color separation can be provided in foundations, cheeks, eyeshadows and the like. Also, the coloring material of the present invention can be used as a cosmetic even in the form of the powders alone, and therefore fats and oils, a surfactant and a preservative are not required to be added thereto, which makes it possible to provide a cosmetic which is less irritant to the skin.

What is claimed is:

1. A highly functional coloring material characterized by coating evenly a pigment on the surfaces of tabular colorless to white inorganic powders which is mica or BN (boron nitride) via a binder resin which is a carboxy betaine resin or an alkali-soluble resin.

2. The highly functional coloring material as described in claim 1, wherein the binder resin is soluble in ethanol and insoluble in water.

3. The highly functional coloring material as described in claim 1, wherein the pigment is an organic pigment, iron oxide, carbon black or fine particle titanium oxide.

4. The highly functional coloring material as described in claim 1, wherein pigments of plural colors are coated on the surfaces of the tabular colorless to white inorganic powders.

5. A production process for the highly functional coloring material as described in claim 1, characterized by comprising the steps of:
   mixing a pigment, a binder resin and a vehicle,
   then dispersing evenly the mixture by means of a disperser,
   then adding tabular inorganic powders to the dispersion and mixing them while stirring and
   taking out the colored tabular inorganic powders by centrifugal separation or filtering and drying and crushing them.

6. A production process for the highly functional coloring material as described in claim 1, characterized by comprising the steps of:
   mixing a pigment, a binder resin and a vehicle,
   then dispersing evenly the mixture by means of a disperser,
   then adding tabular inorganic powders to the dispersion and mixing them while stirring and
   drying the dispersion by means of a spray dryer.

7. The highly functional coloring material as described in claim 1, wherein the pigment not adhered on the inorganic powders is removed.

* * * * *